United States Patent [19]
Kasevich et al.

[11] Patent Number: 6,097,985
[45] Date of Patent: Aug. 1, 2000

[54] MICROWAVE SYSTEMS FOR MEDICAL HYPERTHERMIA, THERMOTHERAPY AND DIAGNOSIS

[75] Inventors: Raymond S. Kasevich, Mount Washington, Mass.; Stuart M. Selkowitz, Etna, N.H.

[73] Assignee: Kai Technologies, Inc., Great Barrington, Mass.

[21] Appl. No.: 09/248,168

[22] Filed: Feb. 9, 1999

[51] Int. Cl.⁷ .................................. A61F 2/00; A61N 1/00
[52] U.S. Cl. .................. 607/102; 607/100; 607/101; 607/156
[58] Field of Search ..................... 607/100, 102, 607/101, 96, 154, 156; 606/33

[56] References Cited

U.S. PATENT DOCUMENTS

| | | | |
|---|---|---|---|
| 4,612,940 | 9/1986 | Kasevich et al. | 128/804 |
| 4,700,716 | 10/1987 | Kasevich et al. | 128/804 |
| 4,776,086 | 10/1988 | Kasevich et al. | 29/828 |
| 5,057,106 | 10/1991 | Kasevich et al. | 606/33 |
| 5,368,591 | 11/1994 | Lennox et al. | 606/27 |
| 5,505,730 | 4/1996 | Edwards | 606/41 |
| 5,916,241 | 6/1999 | Rudie et al. | 607/101 |
| 5,931,860 | 8/1999 | Reid et al. | 607/101 |

*Primary Examiner*—Linda C. M. Dvorak
*Assistant Examiner*—Jocelyn Debra Ram
*Attorney, Agent, or Firm*—Fish & Richardson P.C.

[57] ABSTRACT

Medical systems and instruments which utilize microwave energy to provide heat treatment and diagnostic imaging of tissue are provided. One medical instrument has a collinear array having antennas configured to transmit electromagnetic energy so that the transmitted energy, in aggregate, is directed toward a desired area of the tissue. Another microwave medical system includes a catheter having an inflatable balloon in fluid communication with an inflation source, and an antenna having a radiating element positioned within the inflatable balloon to transmit electromagnetic energy toward the desired area of tissue. Still another medical instrument includes an antenna having receiving elements for receiving electromagnetic energy radiated from an electromagnetic source, rectifying devices, each having a first end electrically connected to a corresponding one of the receiving elements; and a transmission line electrically connected to a second end of each of the rectifying devices.

54 Claims, 13 Drawing Sheets

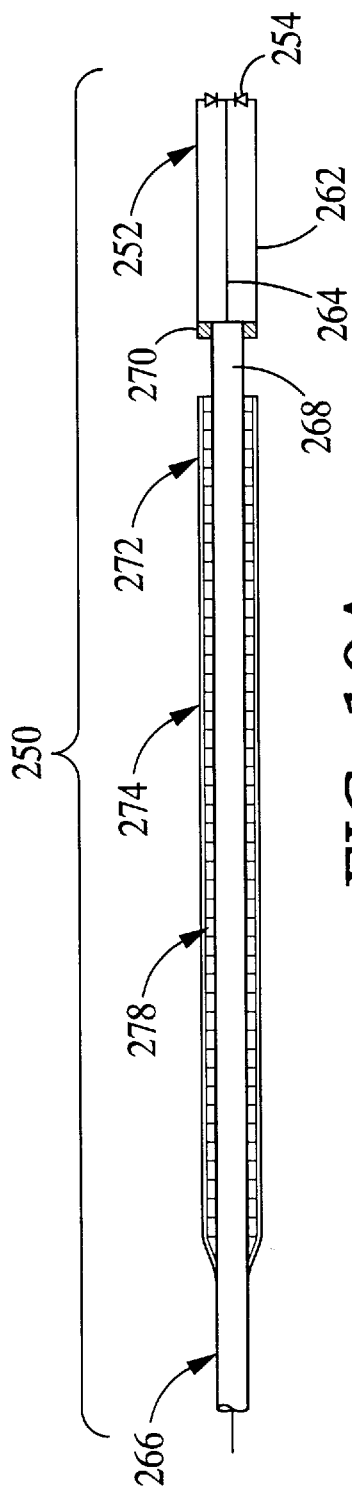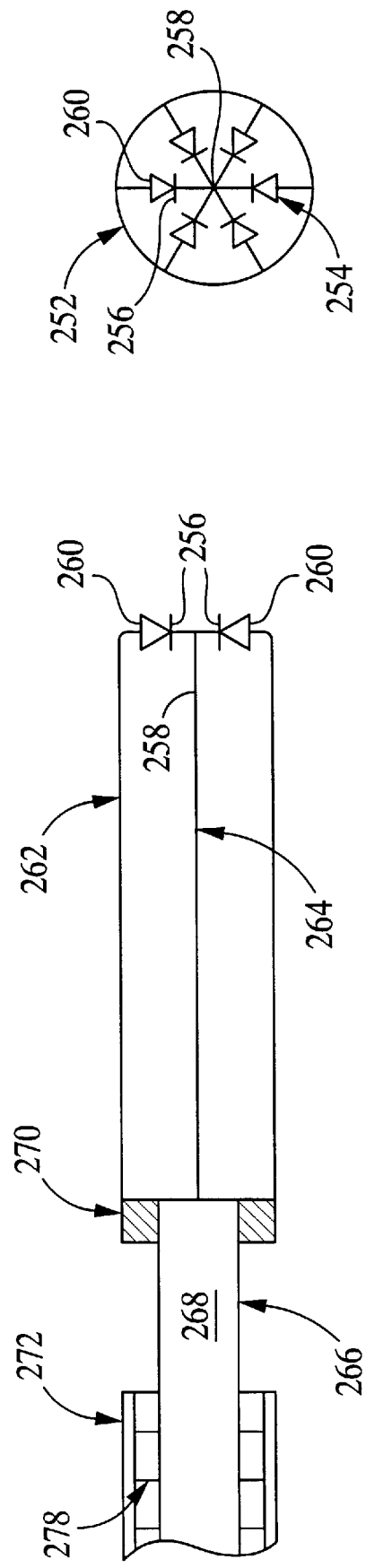
FIG. 10A
FIG. 10B
FIG. 10C

MICROWAVE SYSTEMS FOR MEDICAL HYPERTHERMIA, THERMOTHERAPY AND DIAGNOSIS

BACKGROUND OF THE INVENTION

The present invention relates to microwave devices used in medical hyperthermia and thermotherapy (referred to collectively herein as "heat therapies"), and diagnostics, and to methods of using such devices.

Localized heat therapies, i.e., hyperthermia (heating to temperatures below 45° C.) and thermotherapy (heating to temperatures above 45° C.), have been intensively investigated for the last two decades for many disease processes including benign prostatic hyperplasia (BPH) and neoplasms.

However, methods of delivering heat including warm fluid, focused ultrasound, radio frequency, and microwave approaches have been applied to abnormal tissue with only limited success. The prostate gland is one organ targeted as a candidate for applying heat delivery techniques. Because microwave energy can be applied without incision, this approach is one being evaluated. Furthermore, this technique advantageously can be applied in an outpatient setting.

For heat therapy to be applied safely, it is very important that the applied heat be confined to the target area (e.g., BPH tumor) alone, to avoid damaging nearby healthy tissue or organs.

Some devices for heat therapy have utilized microwave heating, for example those disclosed in U.S. Pat. Nos. 4,700,716 and 4,776,086, the disclosures of which are incorporated herein by reference. Microwave energy elevates temperature by increasing the molecular motion within cell structures. As the frequency decreases, tissue penetration increases. Small diameter microwave antenna probes have been inserted into the body through normal body passages or, on occasion, directly into diseased tissue, using hollow plastic catheters.

SUMMARY OF THE INVENTION

The invention features medical instruments which utilize microwave energy to provide heat treatment and diagnostic imaging of tissue. The term "microwave", as used herein, refers to electromagnetic energy in the microwave frequency spectrum of 300 MHz to 300 GHz.

In one aspect of the invention, the medical instrument includes a collinear array having antennas, each of which is spaced from an adjacent antenna along a longitudinal axis of the array and configured to transmit electromagnetic energy so that the transmitted energy, in aggregate, is directed toward a desired area of the tissue. The medical instrument includes an electromagnetic energy source electrically coupled to the collinear array to provide the electromagnetic energy individually to each of the antennas at a selected amplitude and phase characteristic.

The invention has numerous advantages. For example, the antennas of these medical instruments are arranged, in-vivo, to precisely focus the direction of transmitted electromagnetic energy (e.g., microwave energy), thus allowing well-controlled heating of a target area without substantially heating adjacent non-target areas (e.g., adjacent vital organs or healthy tissue). Because the direction of the applied energy is well-controlled, these instruments require relatively lower amounts of power, e.g., less than 25 Watts, to deliver a high degree of thermal dosimetry, thus ensuring full thermal coverage with a sharp cut-off of the thermal envelope. Because the antennas are arranged in an array, the power deposition pattern of the energy is allowed to be varied by adjusting the voltage amplitude, and phase of the signal supplied to each antenna, thereby effectively beam steering the electromagnetic field to desired areas.

Embodiments of this aspect of the invention may include one or more of the following features.

Each antenna of the collinear array includes a radiating element at the distal end of the array and a coaxial transmission line extending from the radiating element to the proximal end of the array. The coaxial transmission line connects each antenna to the electromagnetic source.

Each antenna includes an impedance matching network coupled between the radiating element and the coaxial transmission line. The impedance matching network includes a conductive shield surrounding the outer conductor of the coaxial transmission line, the conductive shield having a first end electrically connected to the outer conductor and a second end spaced from the first by a distance approximately one-quarter wavelength at the frequency of the transmitted electromagnetic energy.

The medical instrument further includes directing elements positioned adjacent to the radiating elements for enhancing beam steering. These directing elements include an elongated dielectric member extending along the longitudinal axis of the array and having a distal end with an electrically conductive coating.

The medical instrument further includes a temperature detector for sensing the temperature at a location proximate to one of the radiating elements and, in response to the sensed temperature, provides signals to the electromagnetic energy source to control the amplitude and phase characteristics of the energy provided to that one of the radiating elements. In certain embodiments, each antenna has an associated temperature detector.

The medical instrument further includes a catheter having a proximal end, distal end, and an inner lumen extending therebetween, the catheter sized to receive the collinear array. The catheter includes a balloon, at its distal end, formed of a material transmissive of the electromagnetic energy.

The medical instrument further includes a microwave heat pipe having a distal end for withdrawing heat from the target area. The heat pipe includes a conduit having a proximal end connected to a source of coolant (e.g., a condenser) and an enlarged distal portion at the target area. In certain embodiments, a plurality of microwave heat pipes are provided, each associated with a corresponding one of the antennas.

The electromagnetic energy has a frequency in a range between 0.3 and 10 GHz and a power level in a range between about 100 mwatts and 150 watts.

In a related aspect of the invention, a medical heat treatment system includes a pair of medical instruments, each including an antenna system disposed within a catheter, with at least one of the antenna systems being in the form of a collinear array of antennas extending through an inner lumen and positioned at the distal end of an associated one of the catheters. The catheters are of the type having a proximal end, distal end, and a longitudinal axis extending therebetween. The treatment system also includes an electromagnetic energy source electrically coupled to said collinear array to provide the electromagnetic energy individually to each of said plurality of antennas at a selected amplitude and phase characteristic.

In a related aspect of the invention, a method of treating the prostate with the medical treatment system described above, includes the following steps. A first one of the pair of medical instruments is positioned within the urethra. A second one of the pair of medical instrument is positioned within the rectum. Electromagnetic energy is applied to the first of the pair of medical instruments with the second one of the pair of medical instruments receiving the energy after passing through the prostate.

In embodiments of these aspects of the invention, the antenna system that is in the form of the collinear array of antennas is a transmitting antenna system, with the other antenna system being a receiving antenna system.

The treatment system also includes a network analyzer (e.g., scalar or vector) connected to the receiving antenna system, the receiving antenna system receiving signals from the transmitting antenna system. The signals are representative of the material properties of the media positioned between the receiving antenna system and the transmitting antenna system. For example, the signals can be representative of the impedance of the media. Alternatively, the signals can represent the attenuation constant of the media.

In another aspect of the invention, a microwave medical system includes a catheter having an inflatable balloon in fluid communication with an inflation source, and an antenna configured to extend through an inner lumen of the catheter and having a radiating element positioned within the inflatable balloon to transmit electromagnetic energy toward a desired area of tissue.

By positioning the antenna within the inflatable balloon and controlling the level of inflation, the directivity and gain characteristics of the antenna can be advantageously controlled. For example, when the balloon is fully inflated, the antenna is configured to provide a highly focussed, highly directive radiation pattern. Changing the volume of fluid introduced into the balloon changes its dimensions (e.g., diameter). Thus, the radiation pattern of antenna can be altered or modulated by the therapist by inflating and deflating the balloon. The fluid introduced into the balloon can serve as a heat sink for cooling the antenna positioned therein.

Embodiments of this aspect of the invention may include one or more of the following features.

The inflatable balloon includes a surface (preferably the inner surface) having an electrically conductive member formed thereon for directing electromagnetic radiation transmitted by the antenna toward the desired area of tissue. The electrically conductive member may be in the form of a sheet formed on the inner surface of the inflatable balloon or, alternatively, a wire positioned adjacent to the inner surface of the inflatable balloon.

The balloon includes a second electrically conductive member with the first-mentioned electrically conductive member positioned to reflect the electromagnetic energy directed away from the desired area of tissue back toward the tissue and the second electrically conductive member positioned between the antenna and the desired area of tissue. Thus, inflation and deflation of the balloon changes the relative spacing between the antenna and the reflecting and directing conductive members, respectively.

The catheter further includes a second inflatable balloon, which in an inflated condition fixably positions the catheter within a body lumen. This second inflatable balloon, in essence, serves the mechanical function of retaining the catheter in a fixed position, while the first inflatable balloon relates to improving the electromagnetic function of the antenna. The catheter includes a first inflation lumen for providing inflation fluid to the first one of the inflatable balloons and a second inflation lumen, separate from the first inflation lumen, for providing inflation fluid to the second one of the inflatable balloons.

The antenna system includes a first radiating element (e.g., a dipole) having a longitudinal antenna axis and a proximal end coupled to an electromagnetic source; and a second radiating element, in operation, electrically floating relative to electrical ground. The second radiating element includes a conductor helically wound about the longitudinal antenna axis and coaxially positioned around the first radiating element to receive energy radiated by the first radiating element, and an impedance element (e.g., a capacitor) electrically connected between preselected windings of the helically wound second radiating element.

By electrically connecting impedance elements between windings of the radiating element, an antenna system of this configuration is sized to be significantly smaller than a one-half wavelength radiating structure while providing a current distribution similar to that of a one-half wavelength radiating structure.

The first radiating element is moveable with respect to the second radiating element along the longitudinal antenna axis. Thus, the therapist has the ability to optimize the impedance match and, therefore, maximize power transfer from the source to the antenna. Certain embodiments may further include a device for measuring an input impedance characteristic (e.g., reflection coefficient) of the first radiating element, as well as a network analyzer connected to the receiving antenna system. The receiving antenna system receives signals from the transmitting antenna system, said signals representative of the material properties, such as impedance, of the media positioned between the receiving antenna system and the transmitting antenna system.

In still another aspect of the invention, a medical device includes an antenna having receiving elements for receiving electromagnetic energy radiated from an electromagnetic source; rectifying devices, each having a first end electrically connected to a corresponding one of the receiving elements; and a transmission line electrically connected to a second end of each of the rectifying devices.

In essence, the antenna includes a number of rectifying elements (e.g., diodes) having first ends connected to a corresponding receiving element (which may be the leads of the diodes) and second ends connected to a common transmission line. Thus, the rectified outputs for each rectifying device are combined to provide an aggregate rectified current from all of the rectifying devices. The level of current provided by the diodes using this approach is sufficiently high to allow the antenna to be directly connected to many conventional power meters without the need for power amplifiers.

Embodiments of this aspect of the invention may include one or more of the following features. Each of the receiving elements are substantially parallel with the longitudinal axis of the antenna, and circumferentially spaced from each other in a plane transverse to the longitudinal axis of the antenna. The antenna, therefore is far less sensitive to its radial orientation relative to the longitudinal axis of the antenna.

The microwave medical system further includes an impedance matching network coupled between each of the receiving elements and the transmission line. The transmission line is preferably in the form of a coaxial transmission line having a center conductor, an outer conductor, and a dielectric member positioned between the center conductor and the outer conductor.

The microwave medical system includes a catheter sized to receive the antenna and having a temperature detector for sensing the temperature at a location proximate to the receiving elements.

Other features and advantages of the invention will be apparent from the drawings, the following Detailed Description, and the claims.

BRIEF DESCRIPTION OF THE DRAWINGS

FIG. 10A is a cross-sectional view, partially in schematic form, of a survey microwave antenna system.

FIG. 10B is a cross-sectional view, partially in schematic form, of the distal end of the survey microwave antenna system of FIG. 10A.

FIG. 10C is an schematic end view representation of the distal end of the survey microwave antenna system of FIG. 10A.

DETAILED DESCRIPTION

Figure 1:
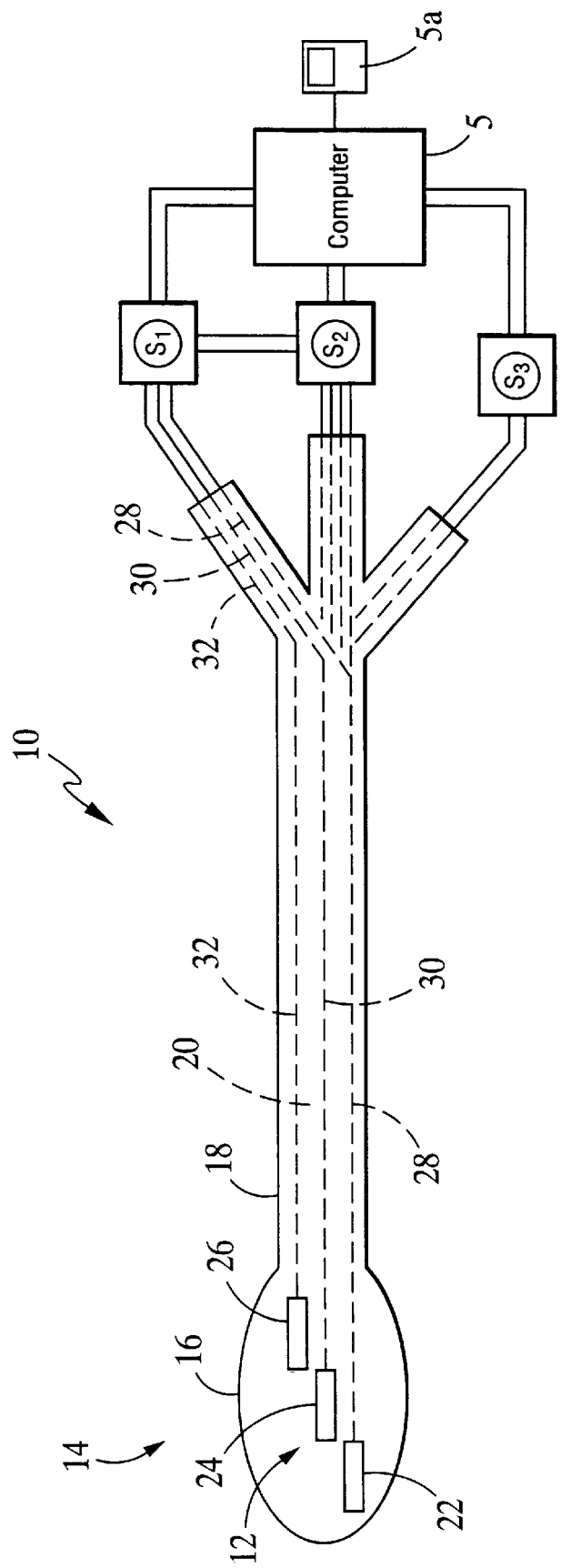
FIG. 1 is a diagrammatic side view of a microwave antenna device according to one embodiment of the invention, deployed in a balloon catheter. Transmission lines are shown in phantom lines.

Referring to FIG. 1, microwave antenna system 10 includes a collinear antenna array 12 deployed within a catheter 14. Array 12 is configured to more precisely focus the direction and level of electromagnetic energy radiating from the array, thereby providing well-controlled heating of the targeted area. Catheter 14 includes a balloon portion 16, mounted at the end of a tube 18, defining an inner lumen 20, and is constructed to be inserted into a portion of the body, typically through a body opening or passage. Antenna array 12 includes three antennas 22, 24, 26, shown in further detail in FIG. 2 and described below.

Figure 3:
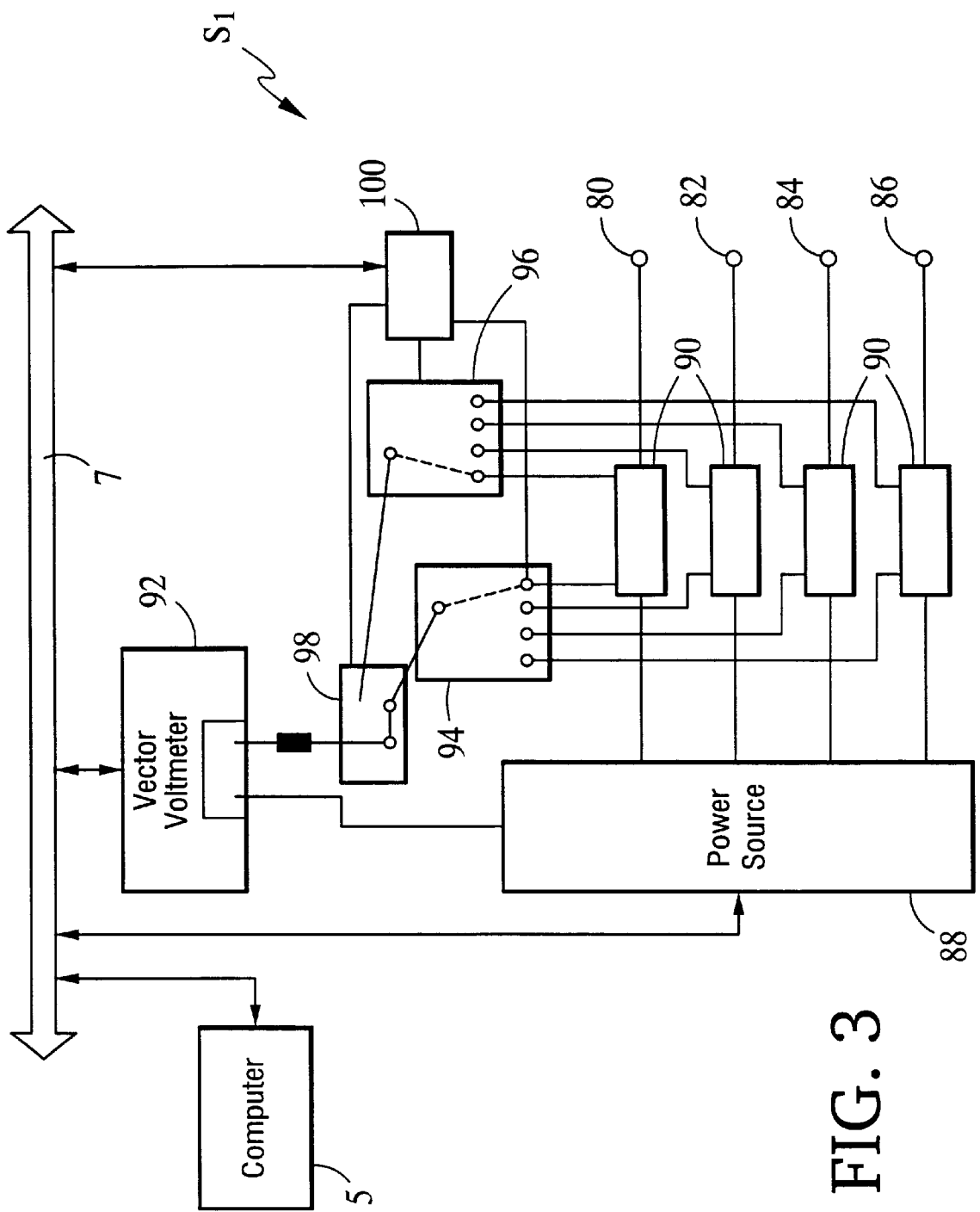
FIG. 3 is a schematic diagram showing the electronics used in a microwave source suitable for use in the device of FIG. 1.

Antennas 22, 24 and 26 are connected via coaxial transmission lines 28, 30 and 32, respectively, to a power system S1 which generates microwave energy. A preferred microwave system S1 is shown in FIG. 3 and discussed below. Electrical signals representative of the temperature measured by sensors 29, 31, 33, and 35 are received and processed by a temperature control unit 52 which generates a control signal to the microwave power system S1. In response to this control signal, microwave power system increases or reduces power delivered to each antenna 22, 24, 26 or array 12. As will be discussed below with reference to FIG. 4, in certain embodiments, a heat pipe S3 is connected to antennas 22, 24, 26 to further control the precise temperature at the device/tissue interface. A computer 5 is connected via a bus 7 to microwave power system S1, temperature control unit S2 and heat pipe system S3. A computer program is stored on computer 5 and, in response to the signals representative of power and temperature, controls power S1, temperature control S2, and heat pipe system S3.

Figure 2:
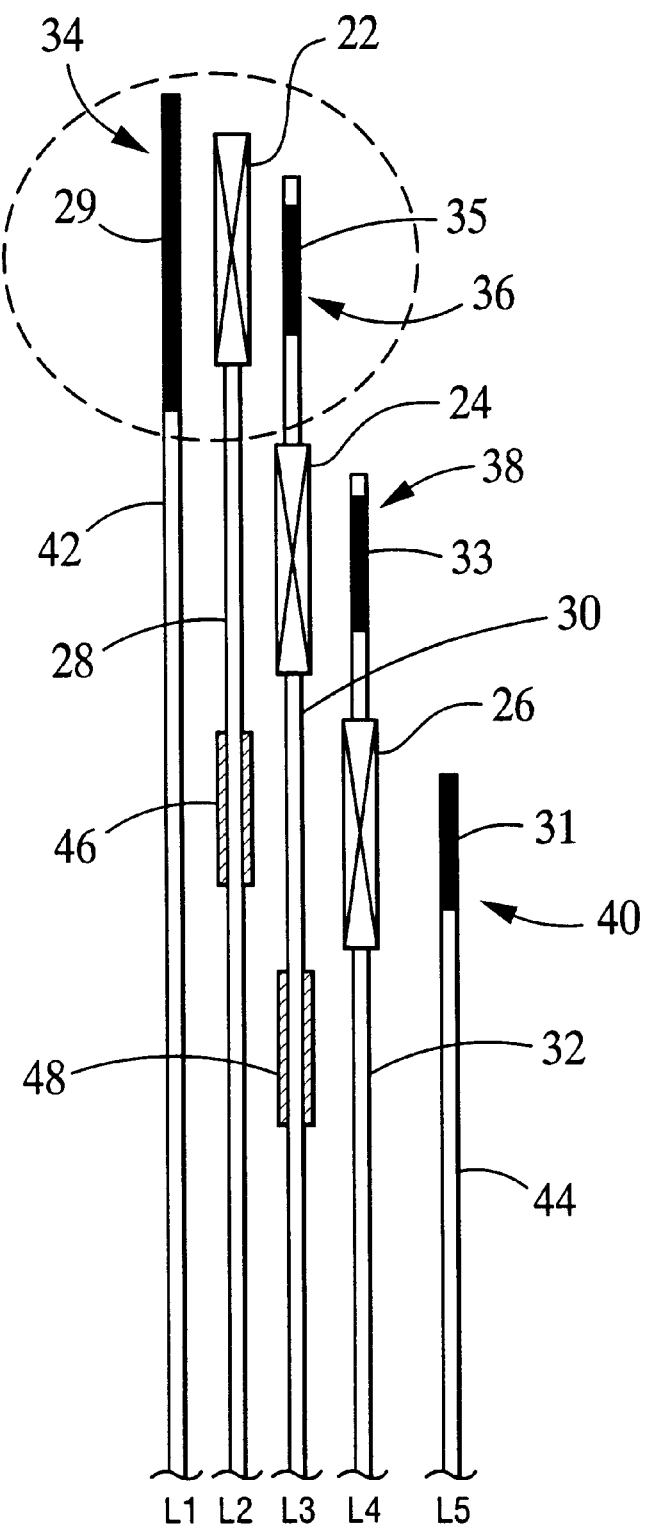
FIG. 2 is a diagrammatic side view of the antennas used in the device of FIG. 1.
Figure 2A:
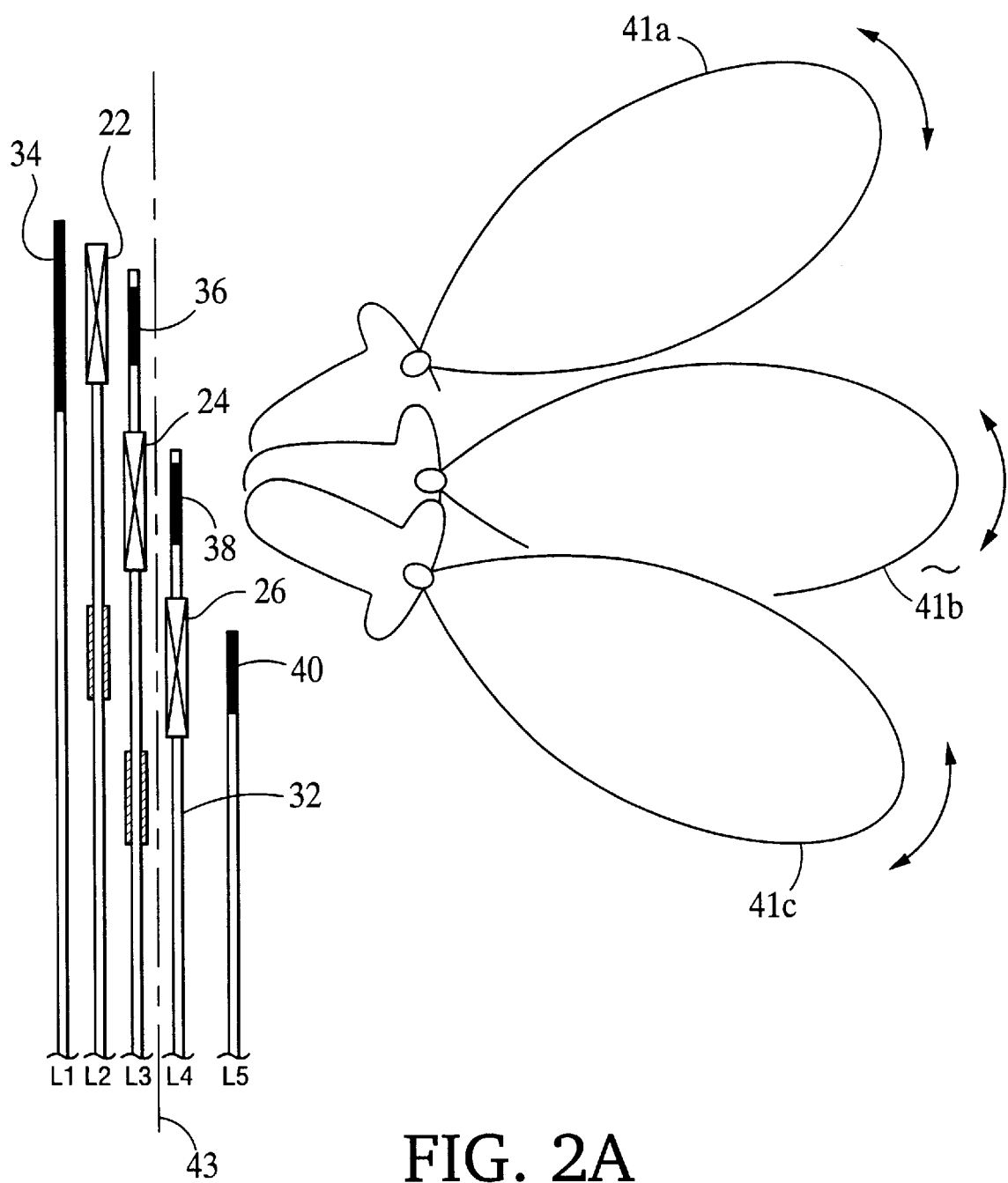
FIG. 2A is a diagrammatic side view of the antennas of FIG. 2, showing the radiation pattern obtained during use.

As shown in FIGS. 2 and 2a, antenna array 12 includes, in addition to antennas 22, 24, 26, an RF reflector 34 and three RF directors 36, 38 and 40. RF reflector 34 and RF director 40 are provided at the end of dielectric members 42, 44 (dielectric wires or tubes), while the other RF directors extend from members attached to distal ends of antennas 24 and 26 on the same coaxial line. The RF reflector and directors are constructed by forming a metallic coating on the dielectric wire or tube. The reflectors and directors serve to further improve the directivity and gain of antennas 22, 24, 26. For example, reflector 34 is positioned behind antenna 22 while director 36 is positioned in front of the antenna to form a three element Yagi array. The lengths of reflector 34 is generally commensurate with the length of the antennas while the lengths of director 36 is generally shorter (e.g., 75% of antenna length.)

Temperature sensors are positioned at various points within antenna array 12. In particular, sensor 29 is positioned at the distal end, sensor 31 at the proximal end, sensor 33 at the center, and sensor 35 along a wall of the antenna array to be positioned at the rectal wall opposite the urethral sensors 29, 31, 33, and 35 may be in the form of fiber optic sensors surrounded by a dielectric outer envelope. One example of a fiber optic sensor of this type is described in U.S. Pat. No. 4,700,716.

Antenna array 12, as well as the RF reflectors and directors shown in FIG. 2, are fixed in position by potting the array in a solid material within a tube, for example, by placing the array in a tube and filling the tube with liquid, hardenable TEFLON® polymer. The tube containing the array can then be easily inserted into the catheter 14 for use by a physician.

As shown in FIG. 2A, each of antennas 22, 24, 26 represent individual radiating elements suitably spaced with respect to one another along a longitudinal axis 43 of catheter 14 to form the collinear array. In preferred embodiments, each antenna is spaced from an adjacent antenna by one-quarter wavelength (λ/4), approximately 1.115 cm at 915 MHz (in tissue with high water content). Although other forms of antennas could be used, in this embodiment, antennas 22, 24, 26 are dipole antennas. The relative amplitude and phase of electrical signals provided to each antenna from microwave system S1 are controlled to obtain a resultant radiation pattern which is the product of the superposition of the radiation patterns from each antenna. In essence, each antenna is independently controlled so that their respective electric fields constructively add within, and destructively subtract outside, the target area. Because the relative amplitude and phase is controlled electronically by microwave system S1, linear array 12 is said to be an electronically-scanned array. With this approach, a radiation pattern with a desired narrow beamwidth and direction provides relatively high temperature and focused heating to the target area.

Furthermore, by varying the relative amplitude and phase of the electrical signals provided to each antenna 22, 24, 26, a radiation pattern can be generated over a relatively broad range. For example, as shown in FIG. 2A, radiation pattern 41 is shown being swept between positions 41a, 41b, and 41c.

To illustrate the improvement achieved by the collinear array arrangement, calculations were made at 915 MHz with antennas 22, 26 in phase opposition to antenna 24. The half power beam width (HPBW) was measured to be 20°, as compared to 45° for a single dipole. A further advantage observed during these measurements was that sidelobes of the resultant radiation pattern were suppressed significantly in lossy media (e.g., tissue with high water content), relative to that observed from a single dipole. This significantly narrower beamwidth allows the user greater flexibility in steering the beam, thereby controlling heating of material.

As shown in FIG. 3, a preferred microwave power system S1 includes four output ports 80, 82, 84, 86, coupled to a four-channel microwave power source 88 capable of providing approximately 12 watts of continuous wave power at 915 MHz to individual ones of antennas 28, 30, 32 of antenna array 12. Note that in this embodiment, because array 12 only includes three antennas, an extra port is available in the event that one of the ports malfunctions. Each port is coupled to a respective output of source 88 through individual bi-directional couplers 90. A fraction (e.g., 20 dB) of the microwave power source 80 is tapped from couplers 90 and provided to a vector voltmeter 92 through a sequence of rotary switches 94, 96, 98. A switch controller 100 is used to select one of ports 80, 82, 84, 86 being examined at any given time. A 30 Db attenuator is connected at the output of rotary switch 98 to protect vector voltmeter 92 from excessive power levels. As stated above, computer 5 is used to control the components of system S1 including, power source 80, vector voltmeter 92 and switch controller 100, via bus 7.

Although not necessary for achieving super-directive radiation patterns, in certain embodiments, each antenna 22, 24, 26 of array 12 can also serve as a "heat pipe". The heat pipe serves as a source or sink for thermal energy at a desired area, so that even greater control of temperature at the interface of the heat pipe and adjacent material is achieved. It is important to recognize that although the device is called a "heat pipe", in operation, it can provide both heating as well as cooling, depending on whether the fluid (e.g., liquid or gas) is hot or cold.

Figure 4:
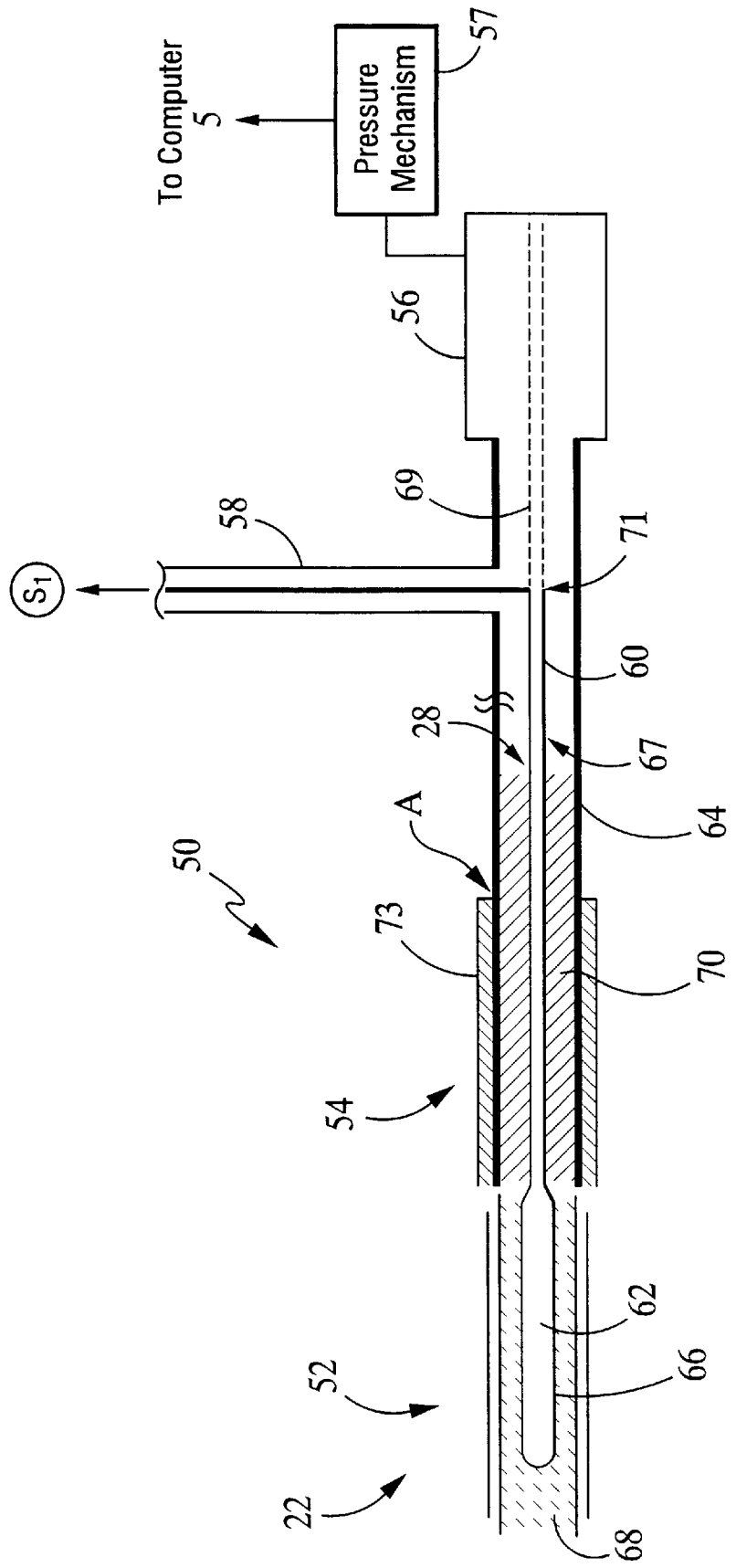
FIG. 4 is a cross-sectional side view of an antenna arrangement suitable for use in the device of FIG. 1, in which one of the antennas also serves as a heat pipe.

Referring to FIG. 4, for purposes of illustration, antenna 22 of array 12 is shown having the structure for providing heat pipe temperature control. Heat pipe 50 includes an antenna portion/cooling region 52, a heat exchanger 56 and a flexible RF coaxial transmission line 58 connecting the antenna portion 52 to microwave power source S1. The antenna portion 52 is formed by a hollow conductive pipe 60 and a dielectric sheath 70 extending substantially the entire length of the conductive pipe. As described above in conjunction with FIGS. 1, 2, 2A, conductive pipe 60 is one part of coaxial transmission line 28 for transmitting energy from source S1 to antenna portion/cooling region 52. When used as a heat pipe, conductive pipe also functions as a capillary wick for a liquid or gas 62 passing therethrough. The capillary action is accomplished by having a relatively larger diameter portion 66 at the antenna portion, to provide evaporative cooling, and a relatively smaller diameter "wick" portion 67 extending between portion 66 and heat exchanger 56. Larger diameter portion 66 is approximately λ/2 in length. At a junction 71, wick portion 67 extends beyond transmission line 58 to the heat exchanger 56 in the form of a dielectric tube 69.

When used in applications where cooling is required, heat exchanger 56 acts as a condenser having a refrigerant (e.g., cryogenic fluid). A pressure mechanism 57 under the control of computer 5 is used to control the amount and rate at which fluid is delivered to cooling region 52. As discussed above, in response to electrical signals from temperature control unit S2, computer 5 controls microwave system S1 to generate electrical signals with the appropriate amplitude and phase characteristics for providing a focused beam in the direction of the target area. In embodiments having a heat pipe 50, computer 5 also controls heat exchanger S3 to convey cooling fluid within antenna portion/cooling region 52 to remove heat, thereby allowing rapid and precise adjustment of the temperature at the interface between the cooling region and surrounding material.

By constructing one or more of antennas 22, 24, 26 as a heat pipe, the relatively high, and focused heating characteristics provided by each antenna of array 12 can be controlled with even greater precision, by quickly and reliably delivering coolant or heat to the target area, thereby decreasing or increasing the temperature, respectively, at the target area. Further details concerning the thermodynamic operation of heat pipes suitable for use in antenna array 12 are described in U.S. Pat. No. 5,591,162, entitled "Treatment Method Using a Micro Heat Pipe Catheter", which is incorporated herein by reference.

In certain applications, antenna array 12 may include transformers 46, 48, positioned between antennas 22, 24 and the microwave power system S1. These transformers present a well-matched impedance to power system S1 within a predetermined frequency range. Transformers 46, 48 are spaced from respective antennas 22, 24 by one-quarter wavelength. Transformer 54 is provided by the combination of conductive pipe 60, an outer conductive coaxial sheath 64, dielectric sheath 70, and a metallic cylinder 73. Outer conductive coaxial shield 64 surrounds dielectric sheath 70 and extends along the length of conductive pipe 60 until terminating at a point just before larger diameter portion 66. Metallic cylinder 73 is approximately one-quarter wavelength in length and covers outer conductive coaxial shield 64, thereby electrically shorting the pair of members at point A. This electrical short presents an effective open circuit (high impedance) along the transmission line one-quarter wavelength away from the short.

Transformer 54 minimizes the reflected power seen by microwave power source S1. Equally important, transformer 54 also prevents leakage of antenna currents along the outside structure of array 12. By appropriate selection of operating parameters, transformer 54 can be designed to provide both a minimum reflection coefficient as well as minimum leakage within the same frequency range.

Using transformers 46, 48 is not limited in an antenna array having a heat pipe. Rather, all of the advantages provided by the use of such transformers, as described above, are achieved when antenna system 10 of FIG. 1 does not include heat pipe system S3.

To use microwave antenna system 10, a physician would insert catheter 14 into a desired region of a patient's body, using a body passage, such as the urethra. The physician would then activate the microwave energy source S1 to deliver energy to a target region adjacent to the body passage. During heating, computer 5 monitors the information collected by temperature control unit S2 and adjusts the amount of energy delivered by microwave power source S1 accordingly. In embodiments which include a heat pipe, computer 5 also controls the delivery of the fluid to the surgical site, such as, by providing appropriate control signals to pressure mechanism 57. The rate of heat delivered is matched to the thermal conductivity of the tissue and the degree to which the tissue is perfused.

Figure 5:
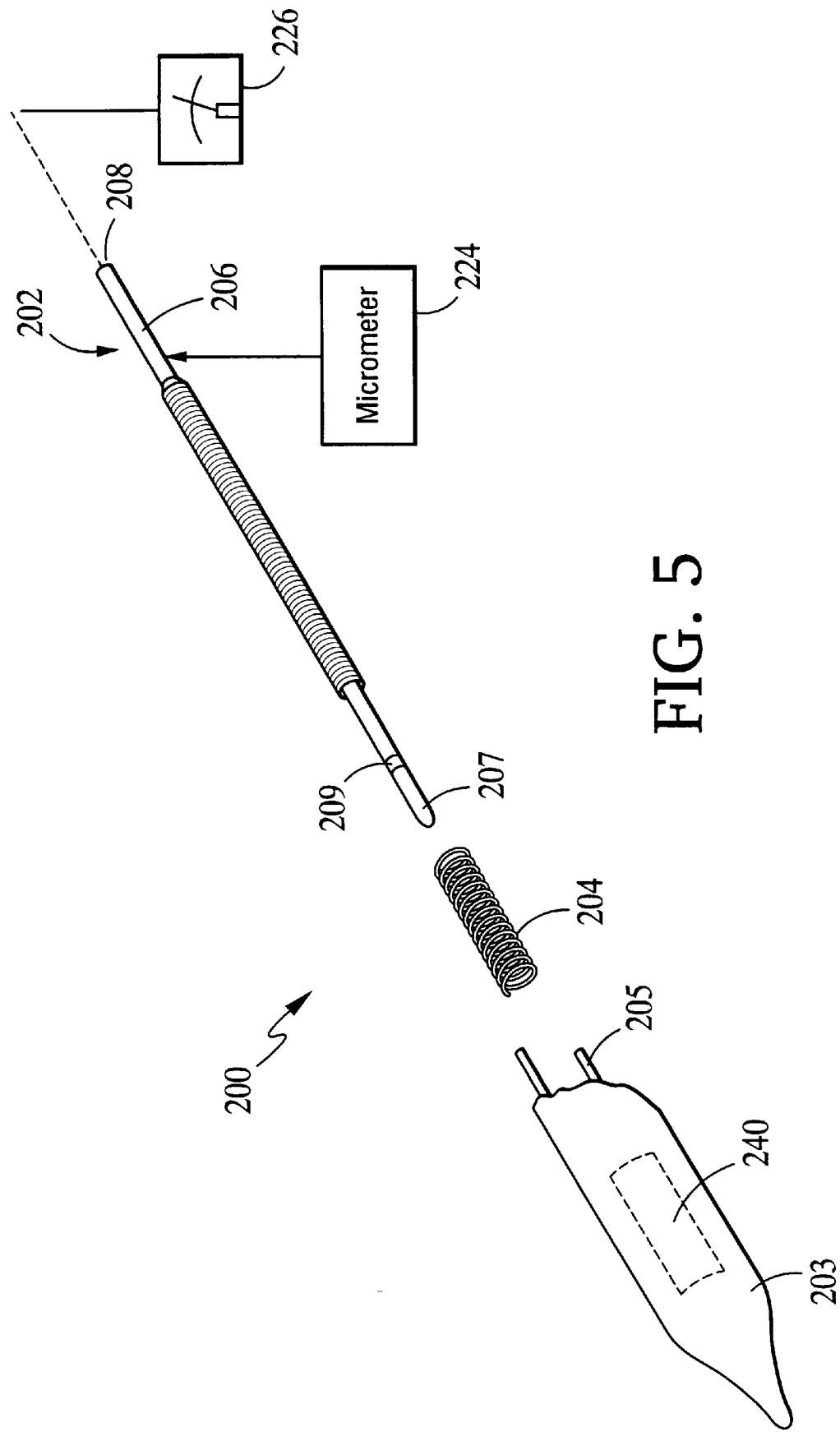
FIG. 5 is a perspective view of an alternative embodiment of an antenna.

Referring to FIG. 5, another embodiment of an antenna 200 well-suited for use within antenna array 12 is shown. It is important to note that although only one antenna is shown, multiple antennas can be extended through a catheter. Antenna 200 includes a pair of radiating elements, one of which serves as a movable exciter dipole 202, the other which serves a magnetic dipole element 204. This configuration allows the surgeon to adjust the position of exciter dipole 202 relative to magnetic dipole element 204 so that both elements radiate together with near-perfect impedance match, thereby maximizing power transfer efficiency to the surrounding tissue. As was the case with the embodiment shown in FIGS. 1–4, antenna 200 is positioned alone or with like antennas within a catheter 205 having an inflatable balloon portion 203.

Figure 6:
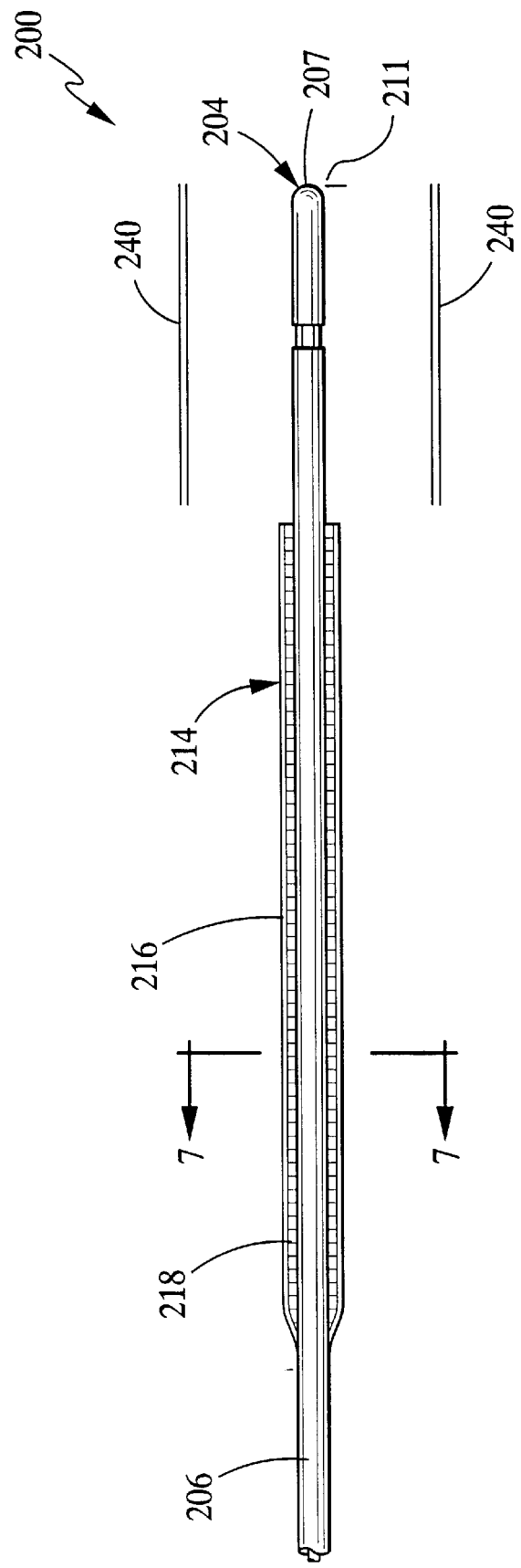
FIG. 6 is a cross-sectional side view of the antenna shown in FIG. 5.
Figure 7:
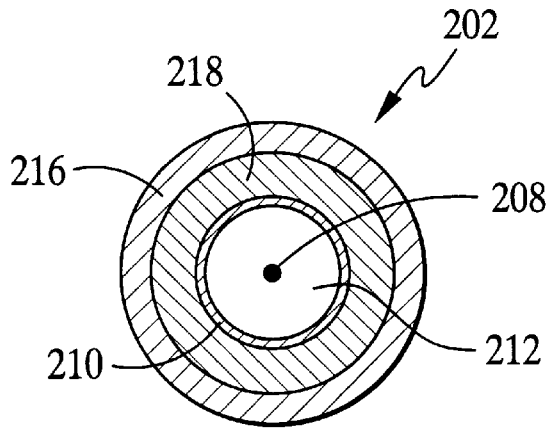
FIG. 7 is a cross-sectional view of the proximal end of the antenna along lines 7—7 of FIG. 6.

Referring to FIGS. 6 and 7, exciter dipole 202 includes a micro-coaxial transmission line 206 which extends from a proximal end 208 connected to a corresponding port of power source S1 to a center-fed dipole element 207. Center-fed dipole 207 is defined by a gap 209 formed by removing a portion of outer conductor 210 at a distance one-quarter wavelength (at the desired frequency of operation) from a distal end 211 of antenna 200.

Transmission line 206 includes a center conductor 208 spaced from an outer conductor 210 by dielectric 212 to provide a transmission line with a characteristic impedance of 50Ω. Exciter dipole 202 also includes a bifurcated impedance transformer 214 defined by a conductive shield 216, which extends along a portion of transmission line 206. Conductive shield 216, which may be braided or in the form of a solid member, is disposed around and spaced from outer conductor 210 of transmission line 206 by a dielectric layer 218. Impedance transformer 214 ensures a good impedance match between center-fed dipole element 207 of exciter dipole 202 and transmission line 206 (50Ω.) A more complete description of the construction and theoretical operation of a similar impedance transformer and its application within a medical instrument can be found in U.S. Pat. No. 4,776,086, entitled "Method and Apparatus for Hyperthermia Treatment", which is incorporated herein by reference.

Figure 8:
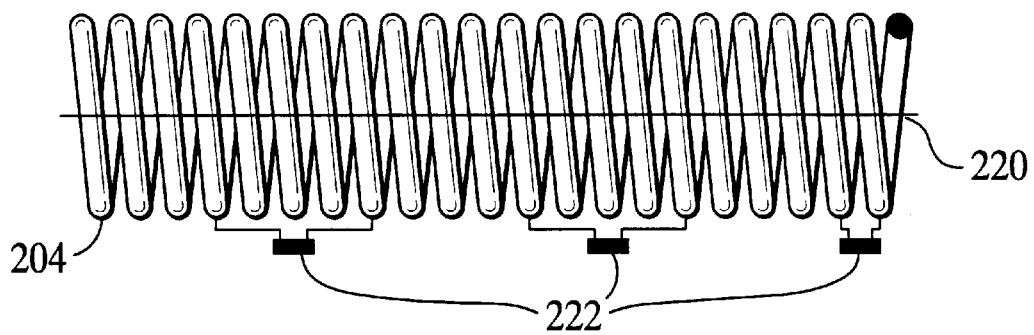
FIG. 8 is a side view of the magnetic dipole of the antenna shown in FIG. 5.

Referring to FIG. 8, magnetic dipole 204 is in the form of a helical winding 213 which, in this embodiment, has 21 turns wound about a longitudinal axis 220 of element 204 and has an inner diameter slightly larger than the outer diameter of center-fed dipole 207. Helical antenna structures similar to helical winding 213 are described in Chapter 7 "The Helical Antenna" of *Antennas* by J. D. Kraus McGraw Hill Publishing Co. (1988), which is incorporated herein by reference. The effects of impedance loading on helical wound antennas is described in Chapter 2 "Wire Antennas" of *Small Antennas* by K. Fujimoto et al., Research Studies Press Ltd. (1987), which is incorporated herein by reference. U.S. Pat. No. 5,755,754, entitled "Device and Method for Asymmetrical Thermal Therapy with Helical Dipole Microwave Antenna", describes an approach for using a helical antenna to thermally treat tissue and is also incorporated herein by reference.

Capacitors 222 are electrically connected between predetermined ones of the turns of helical winding 213. Although helical long wire 213 has a length (L) which is significantly less than one-half wavelength, proper positioning of capacitors 222 along the length of helical winding 213 provides a current distribution resembling a one-half wavelength radiating structure. Without impedance loading, a helical winding of much longer length would be required for resonance and efficient radiation at the desired frequency of operation.

As stated above, because exciter dipole 202 is movable within magnetic dipole 204, the surgeon can axially position exciter dipole 202 to optimize the impedance match between the elements, thereby maximizing microwave energy transfer to the magnetic dipole and, in turn, to the surgical site desired to be heated. Axial movement is critical because the dielectric properties of the tissue itself changes as it is heated, thus causing a change in its impedance characteristics. Thus, the optimum position of exciter dipole 202 relative to magnetic dipole 204 is likely to change as the temperature of the tissue changes. In use, the surgeon adjusts the axial position of exciter dipole using a precise mechanical control mechanism, such as a micrometer 224 (FIG. 5), as he monitors an indicator 226 (FIG. 5) showing the quality of impedance match (e.g., reflection coefficient indicator.) It is important to note that movement of exciter dipole 202 within magnetic dipole 204 can dramatically change the magnitude of the reactance relative to the impedance (e.g., 50Ω) of center-fed dipole 207. However, regardless of the position and the relative reactance magnitude, the current distribution and resulting radiation pattern should be substantially the same.

Figures 9A, 9B:
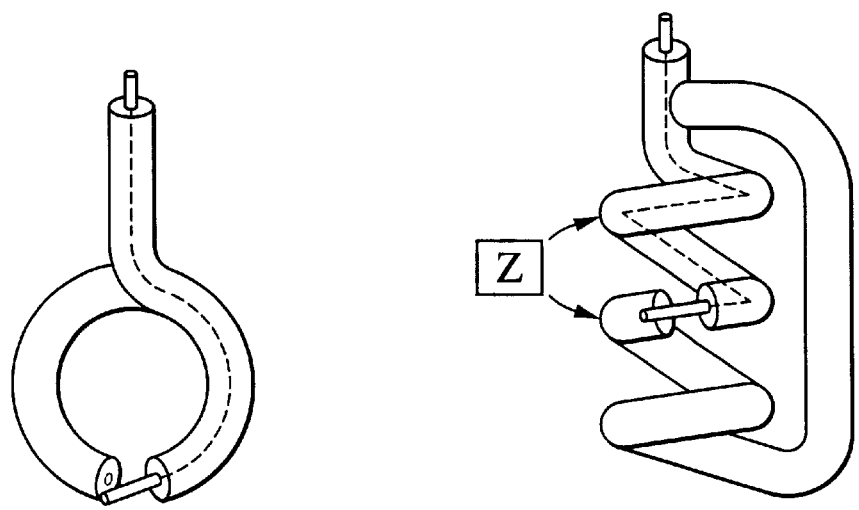
FIGS. 9A and 9B illustrate alternative embodiments of exciter dipoles suitable for use with the antenna shown in FIG. 5.

Referring to FIGS. 9A and 9B, alternative constructions of an exciter dipole 202a, 202b are shown. In particular, exciter dipole 202a is provided in the form of a single turn Faraday shielded loop, while exciter dipole 202b is formed as a multi-turn loop. Exciter dipole 202b may include additional capacitive loading elements connected between one or more loops.

From an electromagnetic wave standpoint, magnetic dipole 204 is floating (i.e., it has no ground plane) and is excited in the $T_0$ mode by exciter dipole 202. Excitation in this manner is similar to exciting a rectangular waveguide in the $TE_{10}$ mode with an electric monopole positioned along the center line of a broad wall of the waveguide.

In use, antenna 200 is introduced to the surgical site through catheter 205. Electrical power is applied to exciter dipole 202 from power source S1. By observing the amount of reflected power on indicator 126, the surgeon adjusts the position of exciter dipole 202 within magnetic dipole 204 using micrometer 224. When the level of reflected power is at a minimum the surgeon is assured that he has found the optimum position.

Referring to FIGS. 10A–10C, a receiving antenna 250 for detecting energy radiated from, for example, antenna 200 is shown. Receiving antenna 250 includes a diode assembly 252 positioned at the distal end of receiving antenna 250. Diode assembly 252 includes rectifying elements in the form of diodes 254, which have their cathodes 256 connected at a common distal node 258. Anodes 260 of the diodes 254 are connected to one of leads 262, which serve as elements for receiving and conveying the electromagnetic wave energy to the diodes. The opposite ends of leads 262 are connected to an outer conductor 268 of a micro-coax transmission line 266 through a conductive washer 270. Each cathode of diodes 254 is connected to a center conductor 264 of micro-coax transmission line 266. Transmission line 266 is of the same construction of transmission line 206 of antenna 200 (see FIG. 6). Specifically, transmission line 266 includes outer conductor 268 spaced from center conductor 264 by dielectric (not shown) to provide a 50Ω characteristic impedance. A bifurcated impedance transformer 272 defined by a conductive shield 274 extends along a portion of transmission line 266. Conductive shield 274, which may be braided or in the form of a solid member, is disposed around and spaced from outer conductor 268 of transmission line 266 by a dielectric layer 278. Impedance transformer 272 ensures a good impedance match between diode assembly 252 and transmission line 266.

Each diode 254 rectifies the electromagnetic waves received along its associated lead 262 and produces a direct current (DC) signal. The current generated by each diode 254 is summed at node 258 and carried to a measurement system (not shown) via coaxial transmission line 266. Diodes 254 may be encapsulated or potted to lend mechanical support to assembly 252.

Referring to FIGS. 11–14, a microwave medical system 300 particularly well-suited for use with antenna 200 is shown. System 300 includes a catheter 302 having an inflatable yagi balloon 304 and an inflatable fixation balloon 306. As will be discussed in greater detail below fixation balloon 306, in operation, is used to mechanically fix the position of the catheter within a body passage, such as the urethra. When positioned in the rectum, a rectal catheter can be fixed in position by external means. On the other hand, yagi balloon 304 is used to control the delivery of energy radiated from antenna 200 to surrounding tissue. In particular, by varying the amount of fluid (e.g., water) and thus, the amount of dielectric material between the radiating antenna and the tissue, the radiation pattern of the energy from antenna is controlled. The fluid can also serve as a heat sink medium for withdrawing heat away from antenna. Indeed, providing additives to the fluid or using a different fluid (e.g., saline) can enhance the heat sinking effect.

In certain applications, the temperature of the fluid or the dielectric constant of the fluid can be controlled to increase the efficacy of the treatment. For example, by changing the salinity of water used to inflate yagi balloon 304, the dielectric constant can be modulated.

In this embodiment, yagi balloon 304 expands symmetrically. However, in certain applications, the balloon can be constructed to expand asymmetrically, for example, with a spacing between antenna 200 and director 330 greater than that between the antenna and reflector 328.

Catheter 302 includes a central passage 308 which is sized to allow antenna 200 to extend to yagi balloon 304. In certain applications, central passage 308 may also be used for passing catheter 302 over a positioning stylet (not shown). A locking mechanism 310 for fixing the position of antenna 200 relative to yagi balloon 304 is provided at the proximal end of catheter 302. A fluid insertion chamber 312 and a fluid extraction chamber 314 surround central passage 308 for allowing cooling fluid to be introduced and withdrawn, respectively, from catheter 302 in the area of yagi balloon 306 during operation of antenna 200.

A lumen 316 extends through catheter 302 from yagi balloon 304 to a syringe valve 318, which is connected to a fluid source (e.g., syringe) for inflating the yagi balloon. A second lumen 320 similarly extends through catheter 302 from fixation balloon 306 to a syringe valve 322, which is connected to a separate fluid source (e.g., syringe) for inflating the fixation balloon. Temperature sensors 324 are attached to an outer surface of catheter 302 and are electrically connected to temperature control unit S2 (FIG. 1) via fiber optic lines (not shown) positioned through lumens 326 extending through the catheter to provide signals indicative of the temperature of the tissue.

As was the case with the embodiment of array 12 shown in FIGS. 1–4, reflector and director elements can be used to further enhance focusing of radiated energy from antenna 200 to a particular area of tissue.

Figure 12:
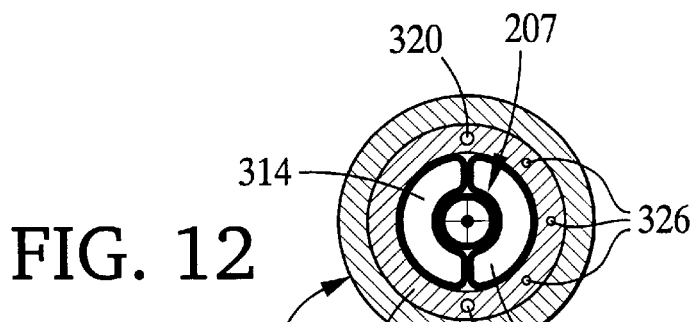
FIG. 12 is a cross-sectional view of the prostate balloon portion of the system shown in FIG. 11 in an deflated condition.
Figure 13:
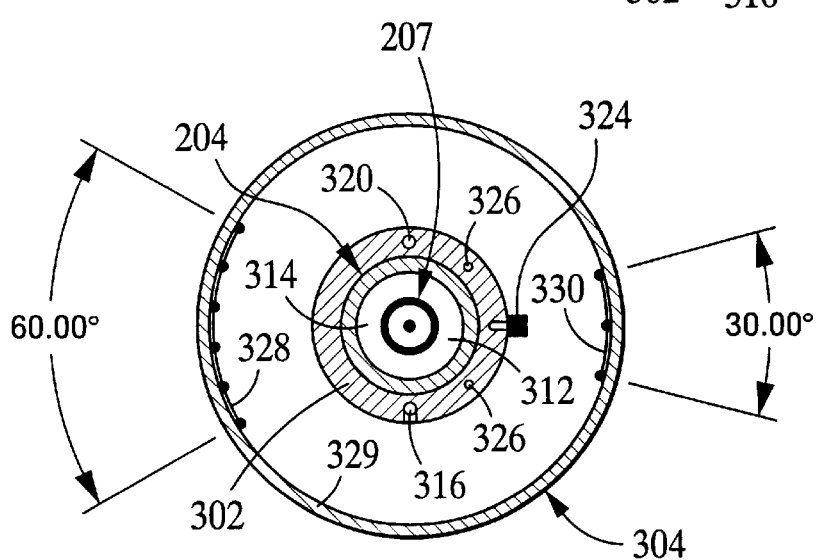
FIG. 13 is a cross-sectional view of the prostate balloon portion of the system shown in FIG. 11 in an inflated condition.
Figure 14:
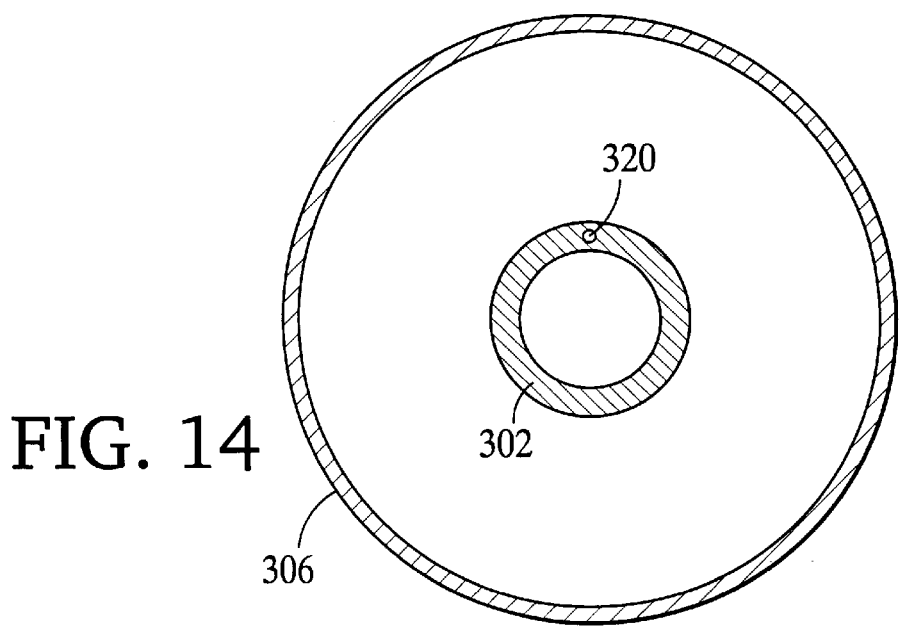
FIG. 14 is a cross-sectional view of the bladder balloon portion of the system shown in FIG. 11 in an inflated condition.

Referring in particular to FIG. 12, in one embodiment, one or more reflectors 328 can be formed along inner surface 329 of yagi balloon 304 to direct any radiated energy incident onto the reflector back toward the desired tissue area. In this embodiment, reflector 328 is in the form of a thin conductive sheet covering an angular area of about 60°. In addition to reflector 328, a director 330 in the form of a conductive sheet is formed on a portion of inner surface 329 diametrically opposite that of reflector 328. Director 330 covers an area of 30°. In alternative embodiments, reflector 328 and director 330 can be in the form of a conductive mesh or set of wires. Changing the volume of fluid within yagi balloon 304, changes the balloon diameter, as well as the relative spacing between antenna 200 and reflector 328 and director 330.

This arrangement of positioning the active antenna element 200 between a reflector 328 and a director 330 provides, in essence, an antenna with increased directivity and higher antenna gain, commonly associated with Yagi antennas. This increased gain characteristic, which can be as much as 6 Db, advantageously allows the required power to antenna 200 to be reduced by a factor of four. Operating at reduced power, allows lower power, less expensive power sources to be used, increases reliability of the source, and provides a significantly safer medical procedure. Furthermore, where higher power is available from the source and is desired for heating, the increased gain characteristic of antenna 200 allows for deeper penetration of heat in tissue (e.g., prostate.)

Figure 15:
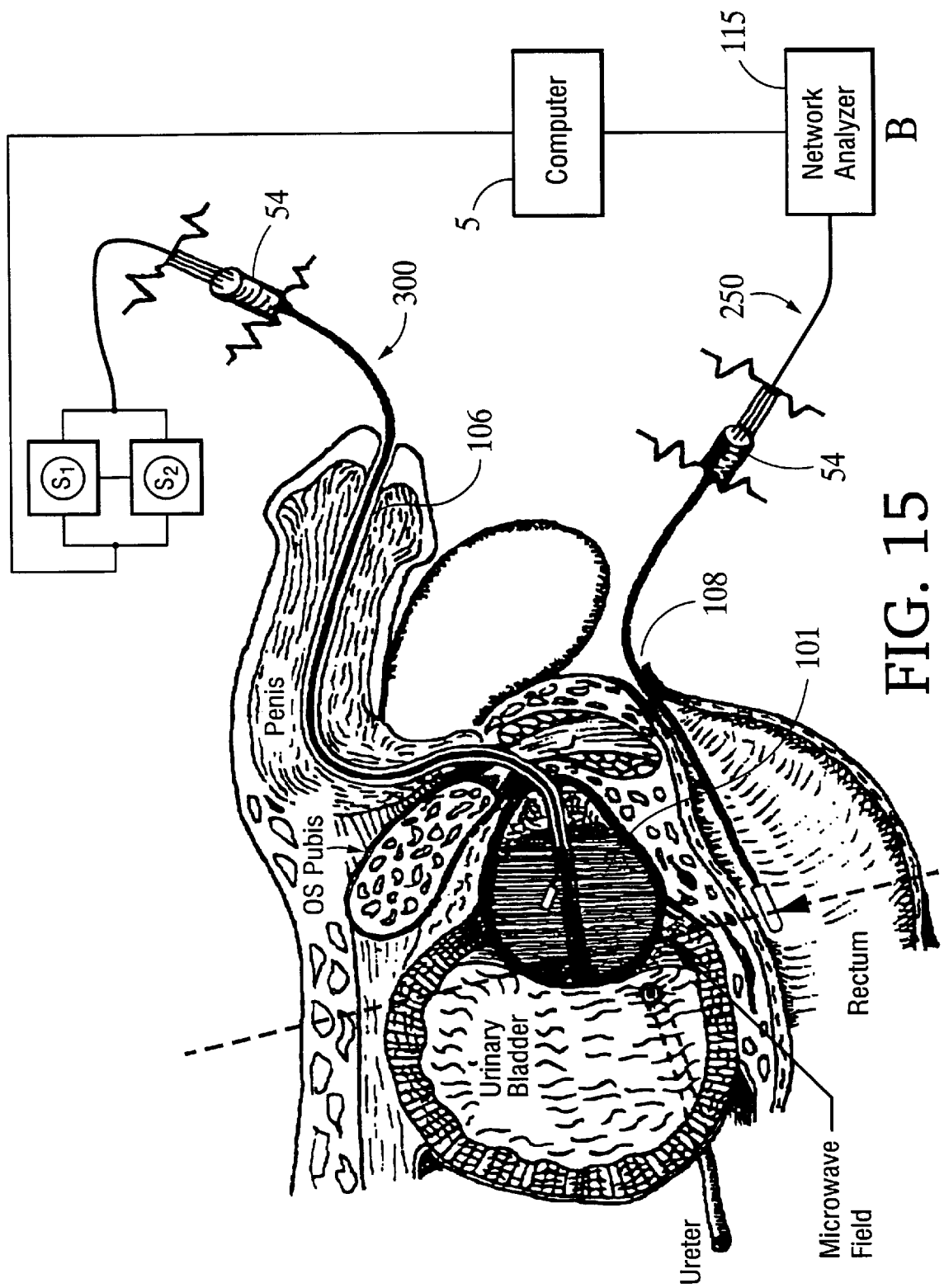
FIG. 15 is a highly diagrammatic view of the male urinary tract, illustrating the use of two microwave antenna devices according to the invention to image and/or heat the prostate gland.

As shown in FIG. 15, microwave antenna system 300 is particularly attractive for use in the treatment and diagnosis of prostatic cancer as well as benign prostatic hyperplasia (BPH). For example, cancer of a prostate 101 often originates on a posterior portion of the prostate close to the rectal wall 102. Thus, system 300 is useful for this treatment because access to prostate 101 can be achieved through the rectum 104 and/or the urethra 106. For example, the physician may insert microwave antenna system 300 within the urethra 106 while positioning receiving antenna 50 through the anus 108 and into rectum 104, as shown. In this application microwave antenna system 300 is used to achieve a high degree of heat uniformity through prostate 101, while receiving antenna 250 monitors the level of energy radiated by antenna system 300.

One approach for treating or diagnosing the prostate using these devices follows. Catheter 302 is first introduced within the urethra and appropriately positioned using well-known positioning techniques, such as ultrasound or more radiopaque markers on catheter 302, so that yagi balloon 304 is positioned adjacent prostate 101. Once positioned, the therapist or surgeon introduces fluid through valve 322 to inflate fixation balloon 306, thereby fixing the position of catheter 302 within the passage.

Antenna 200 is then introduced through central lumen 308 until magnetic dipole 204 and center-fed dipole 207 are both positioned within yagi balloon 304. A relatively low level of power (e.g., 100 mwatts) is then applied to antenna from power source S1. While observing reflection coefficient indicator 226 (FIG. 5), the axial position of exciter dipole 202 is adjusted relative to magnetic dipole 204 until a minimum reflection coefficient is achieved, thereby ensuring maximum transmission power into prostate. The applied power from power source is increased (e.g. 1 to 2 watts) and fluid is then introduced into yagi balloon 304 via valve 318 so that the yagi balloon inflates.

Receiving antenna 250 is introduced within the rectum at a position close to the prostate to detect energy radiated by antenna 200 positioned within urethra 104. Thus, any changes in the radiation pattern of antenna 200 caused by volume of fluid changes in yagi balloon 304 can be detected by receiving antenna 250 and observed, for example, on display monitor 5a. Thus, the radiation pattern of antenna 200 can be altered or modulated by the therapist. In other applications, the level of power applied to antenna 200 from the source can be modulated to control heating of the tissue.

As was stated above, the dielectric constant of the radiated tissue changes due to heating primarily because the amount of fluid in the tissue changes. Thus, it may be desirable during the procedure for the therapist to readjust the axial position of exciter dipole 202 relative to magnetic dipole 204 once again to obtain a minimum reflection coefficient.

Figure 16A:
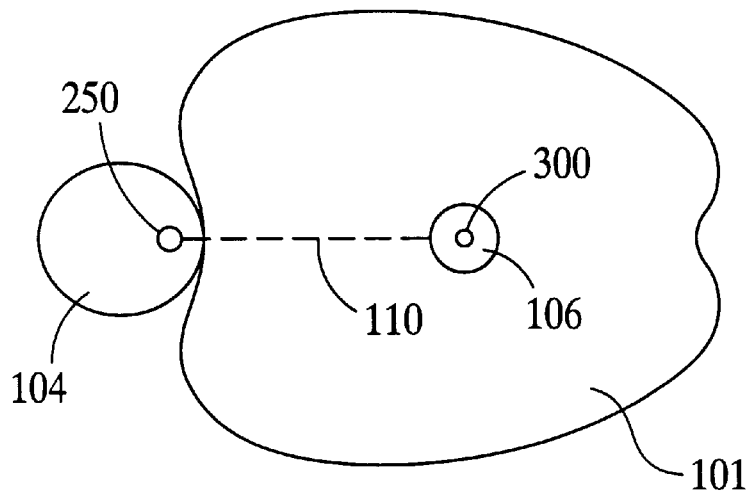
FIGS. 16A and 16B are cross-sectional and side views, respectively, illustrating the use of two microwave antenna devices for imaging and/or heating the prostate gland.
Figure 16B:
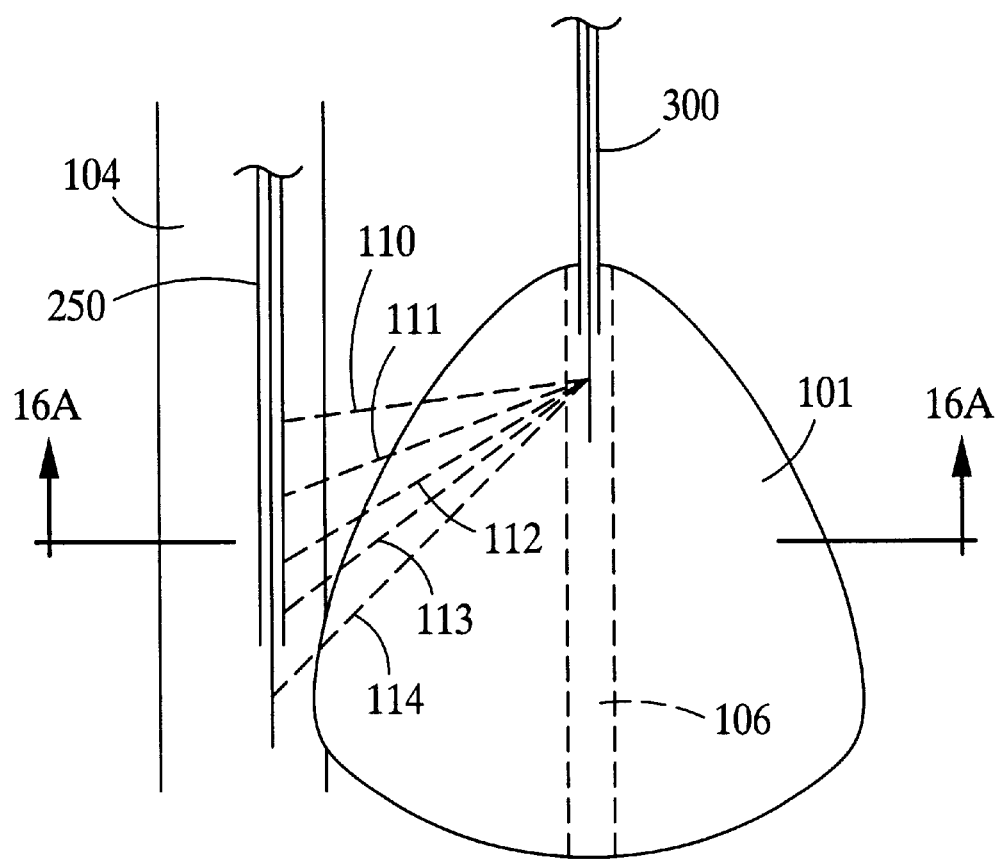

Referring to FIGS. 16A and 16B, a diagnostic approach for using microwave antenna system 300 for treating prostate 101 is shown. In this approach, antenna system 300 is used in a diagnostic mode to locate tissue boundaries, created by the inherent dielectric contrast between abnormal and normal tissues by virtue of their relative water contents.

Figure 11:
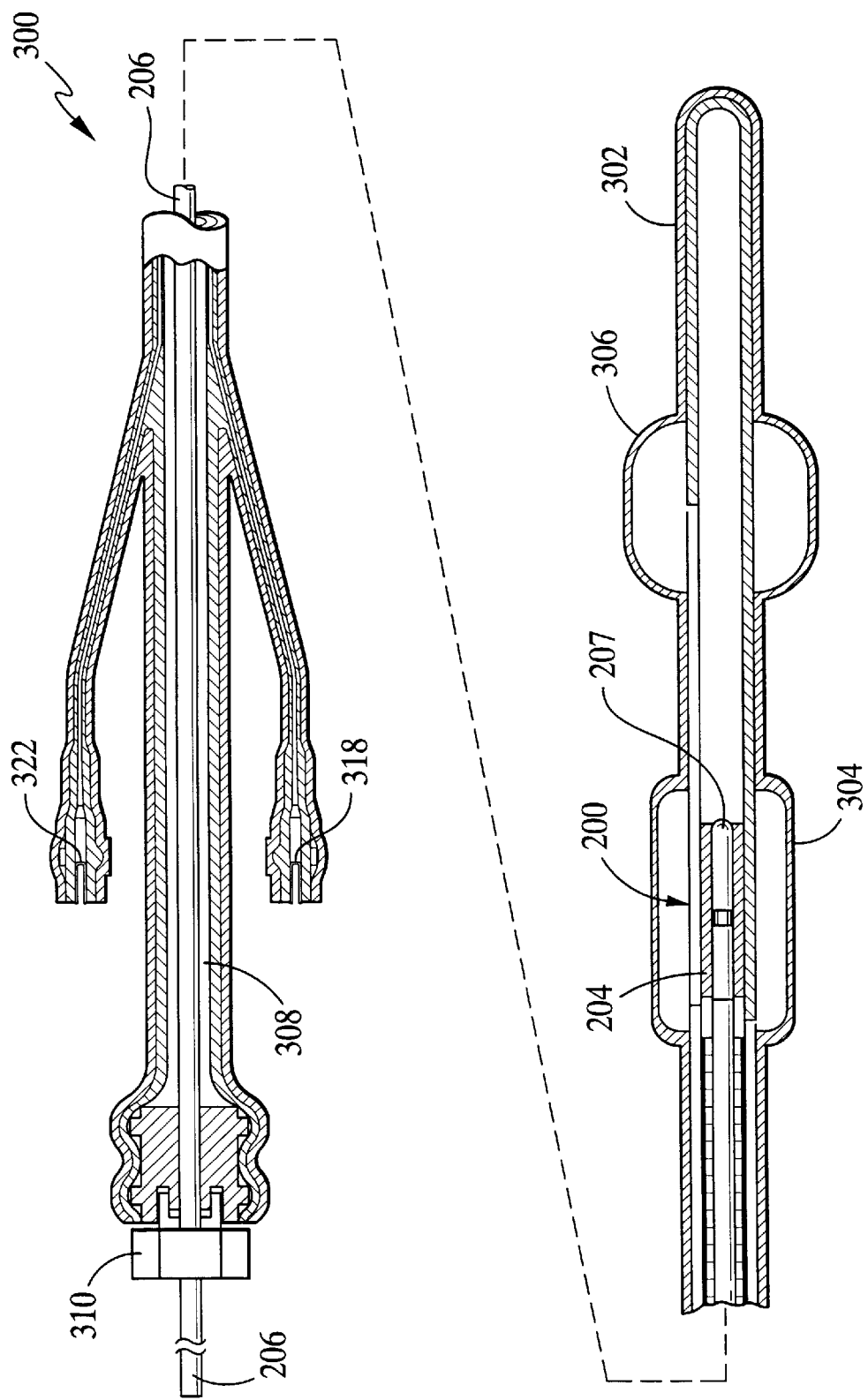
FIG. 11 is a cross-sectional side view of an alternative embodiment of a microwave medical system for treatment and diagnosis of tissue.

In this diagnostic mode, microwave antenna system 300 of the type shown in FIG. 11 is passed through urethra 106 while receiving antenna 250 is introduced into rectum 104. Receiving antenna 250 is used to receive signals transmitted from antenna system 300. The signals transmitted from antenna system 300 are attenuated by the electrical characteristics of the tissue media. Thus, by measuring certain characteristics of the signals as they pass through the tissue, certain material properties of the tissue, such as the electrical attenuation constant ($\alpha$) in Nepers/length can be determined. The attenuation characteristics of the signals passing through the tissue provide an indication as to the type (e.g., bone, muscle, tumor) and relative normalcy of that tissue. For example, healthy muscle tissue typically has less water content than cancerous tissue. Thus, when the narrow beamwidth energy transmitted from antenna system 300 is swept through a region of the healthy tissue and into the neoplastic tissue, as well as through heated and unheated tissue, a change in the value of the attenuation constant is likely to be observed.

In the above described procedure, receiving antenna 250 was positioned within the rectum to detect radiated energy from microwave antenna system 300. In other procedures, a microwave antenna system 300 can be inserted in both rectum 104 and urethra 106 so that prostate 101 is radiated from two different positions.

Computer 5 would generally include a computer display monitor 5a (FIG. 1) for displaying continuous readings of temperature changes at boundaries of a simulated target organ (e.g., prostate) illustration or an ultrasound image. A schematic template of the target organ representing the anatomy would be displayed with superimposed different colors representing different temperature ranges at different regions of the organ. Thus, the therapist or surgeon is able to determine, in real time, the target site and the effectiveness in applying heat from the system. The monitor can display the temperature detected by each of the sensors as a function of time and provide beginning and end points for the treatment.

Based on signals received from the sensors computer 5 is capable of issuing warning messages to be displayed on the monitor when temperatures exceed predetermined threshold values. Computer 5 may also automatically shutdown power source S1 if, for example, the temperatures remain high for an unacceptable time period or if a fault is detected in the system. Computer 5 also includes memory for storing statistical data including patient information, current laboratory data, as well as all data collected during the procedure.

An article by McCorkle et al. entitled "Monitoring a Chemical Plume Remediation via the Radio Imaging Method", which is incorporated by reference, provides a mathematical analysis for determining the electrical attenuation constant.

The antenna systems described above are well-suited for this application because both antenna systems 10 and 300 as well as receiving antenna 250 can remain stationary with the direction of the beam of energy electronically swept through various positions 110–114 by varying the amplitude phase and characteristics of the microwave power source S1. A network analyzer 115 (FIG. 15), for example, an HP 8510 Vector Network Analyzer (a product of Hewlett Packard Company, Palo Alto, Calif.) is connected to antenna system 250 to measure the impedance at the distal end of antenna system 250. The impedance is used to derive the attenuation and phase constant values for each measurement.

It should also be appreciated, however, that a transmitting microwave antenna can be physically moved, for example, by the physician, to provide a series of attenuation characteristic values which can be used to characterize the tissue in the target area. The transmitting antenna can also be rotated about its axis to provide further directional control of the transmitted beam of energy.

Other embodiments are within the scope of the claims.

It is important to appreciate that catheters 14 and 302 can be any of a wide variety of catheters of different configurations and sizes. The particular application in which the microwave antenna system is used will generally dictate the choice of delivery catheter, stylet, as well as the number and particular configuration of antennas. For example, when used in the urethra, flexible foley-type catheters ranging in size between 18–28 F can be used. On the other hand, when introduced into the rectum larger catheters from 22 to 32 F may be more appropriate. The rectal catheter may be accompanied by an ultrasound imaging transducer, both of which are incorporated in a holding sheath. The catheters may include small protrusions positioned along the length of the catheters to facilitate their positioning during delivery. The antennas themselves are radiopaque, as well, to aid in ascertaining their position.

Furthermore, although the above embodiments describe close-ended catheters, alternative applications may require the use of open-ended catheters for end-fire configurations. Additional lumens for introducing irrigation fluids or therapeutic agents (e.g., chemotherapeutic agents, hypothermia, and/or thermal sensitizers) can also be delivered simultaneously or successively to enhance thermal therapy provided by the antennas.

The approach described above utilized the electrical attenuation constant for characterizing tissue. However, other parameters may be derived from the impedance measurements to characterize the tissue as well. For example, the permittivity or complex dielectric constant ($\in^* = \in' - j\in''$) as an indicator of water content in tissue, which, as described above, may be used to determine the type of tissue. With this approach, a calibration procedure is generally required to establish impedance reference values for various known materials, ranging from, for example, distilled water to a sample with no water. Between these two extremes, various types of tissue and neoplasms can be measured with the antenna system to establish a database of impedance values for different tissue.

The ability to use microwave antenna system 10 in a diagnostic mode is a powerful tool, particularly when the antenna system is also used to provide hyperthermia treatment (i.e., in a heating mode). In essence, the diagnostic mode is used to identify and isolate areas which require treatment in the heating mode. Thus, antenna system 10 provides a dynamic, dual-function approach for treating tissue. Use of antenna system 10 in this manner is particularly important when one recognizes that the dielectric properties of tissue change with temperature. By alternating between the heating and diagnostic modes, precise control of the level and direction of heat applied by microwave source can be administered. For example, during heating, the water content of the tissue will decrease and, therefore, the rate at which heat is absorbed by the tissue diminishes. Furthermore, the decrease in water content causes the organ to shrink in size. In the diagnostic mode the change in size and water content will be reflected in a change in impedance, as well as dielectric constant. Based on this change, the amplitude and phase characteristics of the signals applied to each antenna of the array can be altered to more precisely control the direction and level of energy applied to the tumor.

As stated above, in some cases, the impedance of the tissue being treated may change considerably during treatment. If this occurs, the physician may remove the catheter and insert a second microwave antenna device 300 or 10 having different characteristics. For example, a microwave antenna system having slightly different spacings between adjacent antennas may be substituted.

Although, FIGS. 6A and 6B show only a single radiating microwave system 10, it should be appreciated that a separate receiving antenna system 250 allows the use of two or more radiating microwave antenna systems 300 to provide a greater variety of different heating pattern shapes.

For example, while heat pipe S3 has been shown in FIG. 4, and discussed above, as being part of the antenna array, the heat pipe could be provided as a separate device. Moreover, the heat pipe may be operated in such a manner as to iteratively cool and heat the tissue adjacent the antenna.

Also, while FIG. 5 shows the use of a plurality of microwave antenna devices introduced through the urinary bladder and rectum for treatment of the prostate, similar methods can be used in other areas of the body, for example, the liver or kidney.

Still other embodiments are within the scope of the claims.

What is claimed is:

1. A medical instrument for treatment of tissue, the medical instrument comprising:
   a collinear array having a longitudinal axis and a plurality of antennas, each antenna spaced from an adjacent antenna along the longitudinal axis of the array, each antenna configured to transmit electromagnetic energy so that the transmitted energy, in aggregate, is directed toward a desired area of the tissue; and
   an electromagnetic energy source electrically coupled to said collinear array to provide the electromagnetic energy individually to each of said plurality of antennas at a selected amplitude and phase characteristic.

2. The medical instrument of claim 1 wherein each antenna includes a radiating element at a distal end of the array and a coaxial transmission line extending from the radiating element to a proximal end of the array.

3. The medical instrument of claim 2 wherein each antenna further includes an impedance matching network coupled between the radiating element and the coaxial transmission line.

4. The medical instrument of claim 3 wherein the coaxial transmission line includes a center conductor, an outer conductor, and a dielectric member positioned between the center conductor and the outer conductor and the impedance matching network includes a conductive shield surrounding the outer conductor, the conductor shield having a first end electrically connected to the outer conductor and a second end spaced from the first end by a distance approximately one-quarter wavelength at the frequency of the transmitted electromagnetic energy.

5. The medical instrument of claim 2 wherein the medical instrument further includes a plurality of directing elements positioned adjacent to the radiating elements to enhance beam steering.

6. The medical instrument of claim 5 wherein the directing elements include an elongated dielectric member extending along the longitudinal axis of the array, the dielectric member having a distal end with an electrically conductive coating.

7. The medical instrument of claim 2 further including a temperature detector for sensing the temperature at a location proximate to one of the radiating elements and, in response to the sensed temperature, providing signals to the electromagnetic energy source to control the amplitude and phase characteristics of the energy provided to that one of the radiating elements.

8. The medical instrument of claim 7 further including a plurality of temperature detectors, each associated with a corresponding one of the antennas.

9. The medical instrument of claim 1 further including a catheter having a proximal end, a distal end, and an inner lumen extending therebetween, the catheter sized to receive the collinear array.

10. The medical instrument of claim 9, wherein the catheter includes a balloon at its distal end, the balloon formed of a material transmissive to the electromagnetic energy.

11. The medical instrument of claim 9 wherein further including a microwave heat pipe having a distal end for withdrawing heat from a target area of the tissue.

12. The medical instrument of claim 11 wherein the heat pipe includes a conduit having a proximal end connected to a source of coolant and an enlarged distal portion at the target area.

13. The medical instrument of claim 11 wherein the source of coolant includes a condenser.

14. The medical instrument of claim 11 further including a plurality of microwave heat pipes, each associated with a corresponding one of the antennas.

15. The medical instrument of claim 1 wherein the electromagnetic energy has a frequency in a range between 0.3 and 10 GHz.

16. The medical instrument of claim 1 wherein the electromagnetic energy has a power level in a range between about 100 mwatts and 150 watts.

17. A medical treatment system comprising:
a pair of medical instruments, each including an antenna system disposed within a catheter having a proximal end, distal end, and a longitudinal axis extending therebetween, the catheter defining an inner lumen extending along the longitudinal axis and between the proximal end and distal end;
at least one of the antenna systems being in the form of a collinear array of antennas extending through the inner lumen and positioned at the distal end of an associated one of the catheters; and
an electromagnetic energy source electrically coupled to said collinear array to provide the electromagnetic energy individually to each of said plurality of antennas at a selected amplitude and phase characteristic.

18. The medical treatment system of claim 17 wherein a first one of said antenna systems is a transmitting antenna system, a second one of the antenna systems being a receiving antenna system.

19. The medical treatment system of claim 17 further comprising a network analyzer connected to the receiving antenna system, the receiving antenna system receiving signals from the transmitting antenna system, said signals representative of the material properties of the media positioned between the receiving antenna system and the transmitting antenna system.

20. The medical treatment system of claim 19 wherein said signals are representative of the impedance of the media.

21. The medical treatment system of claim 19 wherein said signals are representative of the attenuation and phase constants of the media.

22. The medical treatment system of claim 17 wherein the electromagnetic energy has a frequency in a range between 0.3 and 10 GHz.

23. The medical treatment system of claim 17 wherein the electromagnetic energy has a power level in a range between about 100 mwatts and 150 watts.

24. A method of treating the prostate with the medical treatment system of claim 17, the method including:
positioning a first one of the pair of medical instruments within the urethra;
positioning a second one of the pair of medical instruments within the rectum; and
applying electromagnetic energy to the prostate with the first of the pair of medical instruments.

25. The method of claim 24 wherein the second one of the pair of medical instrument is configured to receive the electromagnetic energy passing through the prostate.

26. The method of claim 24 further comprising applying electromagnetic energy to the prostate with the second of the pair of medical instruments.

27. A microwave medical system comprising:
a catheter including:
an inner lumen extending along a longitudinal axis between a proximal end and a distal end of the catheter;
an inflatable balloon in fluid communication with an inflation source, the inflatable balloon including a surface having a first electrically conductive member formed thereon for directing electromagnetic radiation transmitted by the antenna toward the desired area of tissue; and
an antenna system configured to extend through the inner lumen and having a radiating element positioned within the inflatable balloon, the antenna configured to transmit electromagnetic energy toward a desired area of tissue.

28. The microwave medical system of claim 27 wherein the electrically conductive member is positioned on an inner surface of the inflatable balloon.

29. The microwave medical system of claim 28 wherein the electrically conductive member is in the form of a sheet formed on the inner surface of the inflatable balloon.

30. The microwave medical system of claim 28 wherein the electrically conductive member is in the form of a plurality of wires positioned adjacent to the inner surface of the inflatable balloon.

31. The microwave medical system of claim 27 further comprising a second electrically conductive member, the first electrically conductive member positioned to reflect the electromagnetic energy directed away from the desired area of tissue back toward the tissue, the second electrically conductive member positioned between the antenna and the desired area of tissue.

32. The microwave medical system of claim 27 wherein the catheter further includes a second inflatable balloon, which in an inflated condition fixably positions the catheter within a body lumen.

33. The microwave medical system of claim 32 wherein the catheter includes:
a first inflation lumen for providing inflation fluid to a first inflatable balloon; and
a second inflation lumen, separate from the first inflation lumen, for providing inflation fluid to the second inflatable balloon.

34. The microwave medical system of claim 27 wherein said antenna system includes:
a first radiating element having a longitudinal antenna axis and a proximal end coupled to an electromagnetic source; and
a second radiating element, in operation, electrically floating relative to electrical ground, and including:
a conductor helically wound about the longitudinal antenna axis and coaxially positioned around the first radiating element to receive energy radiated by the first radiating element, and
an impedance element electrically connected between preselected windings of the helically wound second radiating element.

35. The microwave medical system of claim 34 wherein the first radiating element is moveable with respect to the second radiating element along the longitudinal antenna axis.

36. The microwave medical system of claim 34 wherein the helically wound second radiating element has a first diameter and the first radiating element is in the form of a helically wound conductor having a second diameter less than the first diameter.

37. The microwave medical system of claim 34 wherein the impedance element is a capacitor.

38. The microwave medical system of claim 34 wherein the first radiating element is a dipole antenna.

39. The microwave medical system of claim 34 further comprising a device for measuring an input impedance characteristic of the first radiating element.

40. The microwave medical system of claim 34 further comprising a network analyzer connected to the antenna system, the antenna system receiving signals representative of the material properties of the surrounding tissue.

41. The microwave medical system of claim 40 wherein said signals are representative of the impedance of the media.

42. The microwave medical system of claim 34 wherein the electromagnetic energy has a frequency in a range between 0.3 and 10 GHz.

43. The microwave medical system of claim 34 wherein the electromagnetic energy has a power level in a range between about 100 mwatts and 150 watts.

44. A medical device comprising an antenna having a longitudinal axis and including:
   a plurality of receiving elements for receiving electromagnetic energy radiated from an electromagnetic source;
   a plurality of rectifying devices, each rectifying device having a first end electrically connected to a corresponding one of the plurality of receiving elements; and
   a transmission line electrically connected to a second end of each of the rectifying devices.

45. The microwave medical system of claim 44 wherein each of the receiving elements are substantially parallel with the longitudinal axis of the antenna, and circumferentially spaced from each other in a plane transverse to the longitudinal axis of the antenna.

46. The microwave medical system of claim 44 further comprising an impedance matching network coupled between each of the receiving elements and the transmission line.

47. The microwave medical system of claim 44 wherein the transmission line is a coaxial transmission line having a center conductor, an outer conductor, and a dielectric member positioned between the center conductor and the outer conductor.

48. The microwave medical system of claim 44 wherein each of the rectifying devices is a diode.

49. The microwave medical system of claim 48 wherein each of the receiving elements is formed by a lead portion of each of the diodes.

50. The microwave medical system of claim 44 further comprising a catheter having a proximal end, a distal end, and an inner lumen extending therebetween, the catheter sized to receive the antenna.

51. The medical instrument of claim 50 wherein the catheter further includes a temperature detector for sensing the temperature at a location proximate to the receiving elements.

52. The microwave medical system of claim 50 further comprising a network analyzer connected to the transmission line for receiving rectified signals from the rectifying elements representative of the material properties of the media positioned between the antenna and the electromagnetic source.

53. The microwave medical system of claim 52 wherein the analyzer is configured to receive signals from the temperature detector representative of the temperature at a location proximate to the receiving elements.

54. The medical instrument of claim 50 wherein the catheter further includes a temperature detector for sensing the temperature at a location proximate to the receiving elements.

* * * * *